United States Patent [19]

Okorodudu et al.

[11] Patent Number: 5,182,036
[45] Date of Patent: Jan. 26, 1993

[54] BORATED HYDROXYALKYL ESTERS OF ALKYL- OR ALKENYLSUCCINIMIDE-DERIVED DITHIOCARBAMIC ACIDS AS MULTIFUNCTIONAL ASHLESS DISPERSANTS

[75] Inventors: Abraham O. M. Okorodudu, West Deptford; Angeline B. Cardis, Florence, both of N.J.

[73] Assignee: Mobil Oil Corp., Fairfax, Va.

[21] Appl. No.: 766,305

[22] Filed: Sep. 27, 1991

[51] Int. Cl.$^5$ ............... C10M 133/44; C10M 135/18
[52] U.S. Cl. ............... 252/47.5; 252/49.6; 558/295; 548/545
[58] Field of Search ............ 252/47.5, 49.6; 548/545; 558/295

[56] References Cited

U.S. PATENT DOCUMENTS

| | | | |
|---|---|---|---|
| 4,859,356 | 8/1989 | Okorodudu | 252/47.5 |
| 4,957,643 | 9/1990 | Lam | 252/47.5 |
| 4,965,005 | 10/1990 | Camenzind | 252/47.5 |
| 4,985,156 | 1/1991 | Ashjian et al. | 252/49.6 |
| 5,049,293 | 9/1991 | Blain et al. | 252/49.6 |
| 5,068,045 | 11/1991 | Doner et al. | 252/49.6 |

*Primary Examiner*—Jacqueline Howard
*Attorney, Agent, or Firm*—Alexander J. McKillop; Malcolm D. Keen; Howard M. Flournoy

[57] ABSTRACT

Borated hydroxyalkyl esters of alkyl- or alkenylsuccinimide-derived dithiocarbamic acids, have been found to be effective multifunctional additives in lubricant and fuel applications.

19 Claims, No Drawings

BORATED HYDROXYALKYL ESTERS OF ALKYL- OR ALKENYLSUCCINIMIDE-DERIVED DITHIOCARBAMIC ACIDS AS MULTIFUNCTIONAL ASHLESS DISPERSANTS

BACKGROUND OF THE INVENTION

1. Field of the Invention

This invention is directed to novel borated hydroxyalkyl esters of alkyl- or alkenylsuccinimide-derived dithiocarbamic acids as multifunctional ashless dispersants and to lubricant compositions containing same.

2. Description of Related Art

N,N-diorganodithiocarbamates (mostly as metal salts, e.g., antimony, zinc, etc.) are commercially available as multifunctional antioxidant, antiwear and corrosion inhibitor additives. However, materials such as 4,4'-methylenebis (dibutyldithiocarbamate) have been variously described in the literature as EP/antiwear/rust inhibiting; EP/antiwear; sludge dispersant/antiwear/rust inhibiting and antiwear/friction reducing compositions. Also, mixtures of this material admixed with other additives are commercially available in compositions described as antioxidant and antiwear additives. See U.S. Pat. Nos. 4,879,054, 4,655,949 and 4,648,885. Furthermore, it is known that ashless thiophosphates derived from dithiocarbamates are effective multifunctional antiwear/antioxidant additives for lubricants. Similarly, alkyl- or alkenylsuccinimides are well known in the art as ashless dispersants for lubricants and fuels, in which capacity they function primarily as dispersants to minimize sludge accumulation on engine parts.

BRIEF SUMMARY OF THE INVENTION

This application and the invention which it discloses are directed more particularly to novel borated alkyl- or alkenylsuccinimide-derived dithiocarbamates. The synergistic combination of the succinimide and the dithiocarbamate moieties in the products of this invention provides ashless dispersants with additional multifunctional antioxidant and antiwear protection for lubricant compositions. These novel compositions may also provide beneficial cleanliness, metal deactivating, and stabilizing properties to fuels. To the best of our knowledge, the syntheses and lubricant and fuel applications of this class of compounds have not been disclosed elsewhere and are, therefore, novel. This application is thus also directed to improved lubricant compositions comprising the described additives and to fuel compositions containing same.

It is, therefore, an object of this invention to provide improved lubricant compositions, novel multifunctional lubricant additives, and to a process of using such additive products of reaction in such compositions. It is also an object of this invention to provide improved fuel compositions.

DESCRIPTION OF THE PREFERRED EMBODIMENTS

Dispersant alkyl- or alkenylsuccinimides are readily converted to novel dithiocarbamates by reaction with carbon disulfide in the presence of an organic or inorganic base. Boration of the β-hydroxyalkyl esters formed as adducts of these dithiocarbamates by reaction with olefin oxides provides ashless dispersants with multifunctional antioxidant, load carrying as well as potential friction modifying properties in lubricating oil compositions.

The tertiary amine, e.g., triethylamine salts of N,N-diorganodithiocarbamic acids are readily prepared by reacting equimolar amounts of triethylamine, a secondary amine and carbon disulfide in an organic solvent such as toluene or hexane, according to Equation 1. Similarly, the sodium salts are prepared by using sodium hydroxide instead of the tertiary amine, as shown in Equation 2.

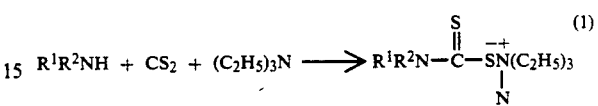

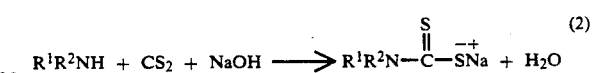

The β-hydroxyalkyl esters may then be prepared by reacting these salts with a hydrocarbylene oxide or mixture of hydrocarbylene oxides as shown in Equation 3.

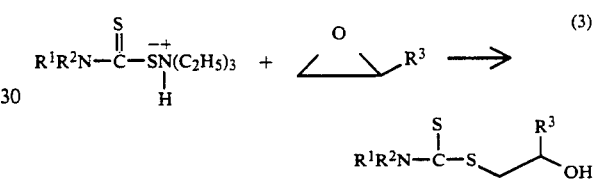

Other reaction schemes can be used to obtain the same desirable intermediates. The borated products may then be obtained by reacting the β-hydroxyalkyl esters with boric acid (or any other convenient borating agent, such as a trihydrocarbyl borate), as shown in Equation 4.

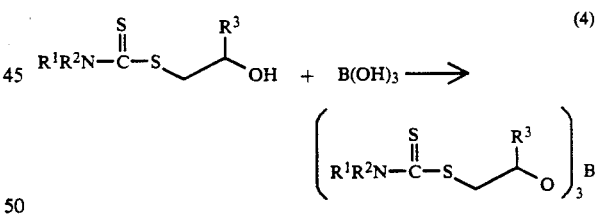

$R^1$, $R^2$ are the same or different and are each a hydrocarbyl group containing from 1 to 36 carbon atoms, having none or at least one heteroatom which can be sulfur, oxygen or nitrogen;

$R^1$, $R^2$ are selected from alkyl, aryl, alkaryl, arylalkyl groups which can contain phenyl, naphthyl or anthryl substituents;

$R^1$, $R^2$ can be (CHn)m group comprising part of an alicyclic or heterocyclic system selected from, for example, pyrrole, pyrrolidine, piperidine, morpholine, etc., where n is 1 or 2, and m is 2 to 50.

In the present application, the above chemistry is extended to alkyl- or alkenyl-substituted succinimides.

Dispersant alkyl- or alkenyl-substituted succinimides are prepared by aminating the corresponding anhydrides with polyamines, viz:

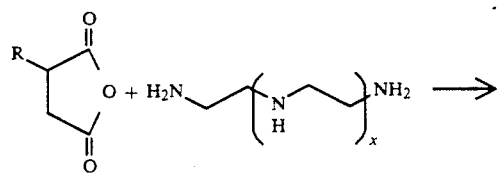

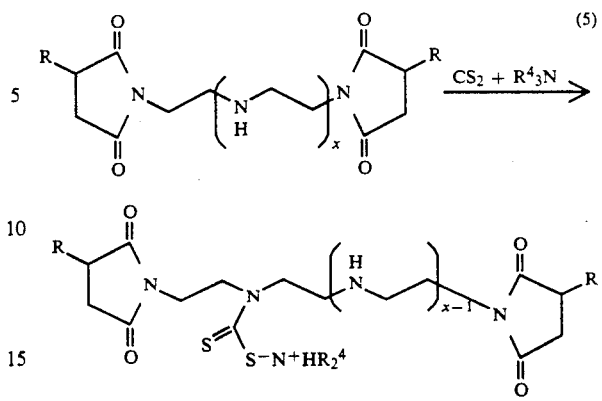

Post-reaction of the succinimides with carbon disulfide in the presence of a tertiary amine, e.g., triethylamine, in an organic solvent such as toluene, provides the quaternary amine salt of the corresponding succinimide-substituted dithiocarbamic acid, according to Equation 5.

From 1 to x equivalents of carbon disulfide and tertiary amine may be used per equivalent of the succinimide, wherein x is the number of basic nitrogens present in the succinimide, and can be an integer from 1 to 10, or mixtures thereof.

The β-hydroxyalkyl esters may then be prepared by reacting these salts with hydrocarbylene or alkylene oxides as shown in Equation 6.

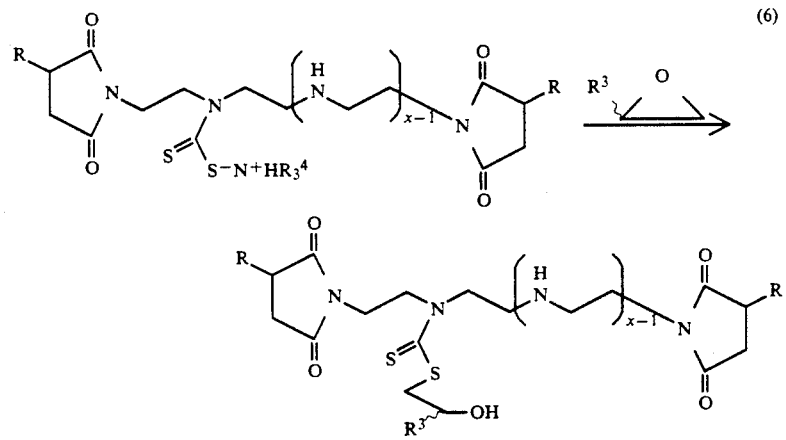

The borated products of this invention may then be obtained by reacting the β-hydroxy esters with boric acid as shown in Equation 7.

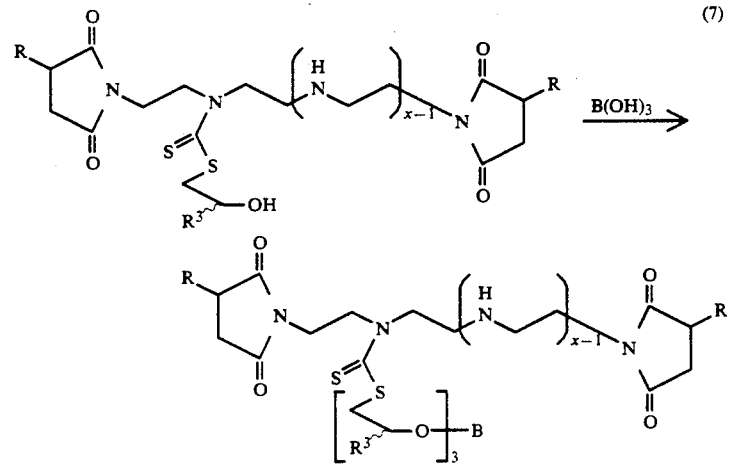

In the above equations:

R=Alkyl or alkylene group containing from 8 to 10,000 carbon atoms.

$R_3$=Hydrogen, alkyl or alkenyl group containing from 1 to 100 carbon atoms, aryl, alkylaryl or arylakyl groups.

$R_4$=Hydrocarbyl or hydrocarbylene part of a tertiary amine such as triethylamine, and tributylamine, mixed alkyl tertiary amines, mixed alkyl/aryl tertiary amines, pyridine, hexamethylene tetramine, etc.

Any suitable tertiary amine may be used. Preferred are trialkylamines, $C_1$ to about $C_{12}$ such as triethylamine, tributylamine and the like.

Conditions for the above reactions may vary widely depending upon specific reactants, the presence or absence of a solvent and the like. Any suitable set of reaction conditions known to the art may be used. Hydrocarbon solvents such as toluene or xylenes are frequently used. Generally stoichiometric or equimolar ratios of reactants are used. However, more than molar or less than molar amounts may be used. In any event, reaction conditions are not viewed as critical. Preferably, however, the molar ratio of succinic anhydride to polyamine varies from 2:1 to about 1:1 and the molar ratio of $CS_2$ to tertiary amine to succinimide varies from 1 to x per mole of succinimide, x=1 to 10, under ambient or autogenous pressure at temperature of under 40°-45° F.

Clearly the use of these borated hydroxyalkyl esters of alkyl- or alkenylsuccinimide derived dithiocarbamic acids derived provide exceptional antiwear and antioxidant activity with potential rust inhibiting properties. Any suitable method of boration may be used in addition to the boric acid method. For example, transesterification using a trialkyl borate such as tributyl borate. Also boric oxide and metaborates may be used. Generally speaking the useful boron compounds are included in the general structure:

$$[(RO)_p(BO_2)_q Y_n Z_r]$$

wherein R, Y and Z are hydrogen or alkyl groups containing 1 to 6 carbon atoms, p, n and r are 0 to 2 and q is 1 to 3. Included within the formula are boric acid, metaboric acid, the alkyl metaborates, the alkyl boroxines, boroxine, boroxides and the like.

Any suitable tertiary amine may be used. Trialkyl amines such as tributylamine and triethylamine are preferred. Similarly, any suitable polyamine may be used in the process of this invention. Preferred are polyalkylene polyamines such as diethylenetriamine and triethylenetetramine characterized as "amine dispersants" and described, for example, in U.S. Pat. Nos. 3,275,554; 3,438,757 and 3,565,804.

The alkyl- or alkenyl substituents of the succinic anhydrides include but are not limited to those having from 1 to about 10,000 carbon atoms. They are usually prepared from olefins having an MW of from about 400 to about 3000.

Any suitable hydrocarbylene oxide, preferably as described in equation 3 above, may be used, such as ethylene oxide, propylene oxide, styrene oxide and the like.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 6 wt. %. It is expected that these materials would also be suitable for use in liquid hydrocarbyl or alcoholic or mixed hydrocarbyl/alcoholic fuel or oxygenated fuel compositions. They are utilized in fuels in amounts of from about 25 to 500 pounds of additive per thousand barrels of fuel and preferably from about 50 to about 250 pounds per thousand barrels of fuel.

The additives have the ability to improve the antiwear characteristics and friction reducing characteristics of various oleagenous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as, for example, from about 45 SSU at 100° F. to about 6000 SSU at 100° F. and preferably, from about 50 to about 250 SSU at 210° F. These oils may have preferred viscosity indexes ranging to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

The fuels contemplated are liquid hydrocarbon combustion fuels, including oxygenated and alcoholic fuels and mixtures thereof as well as distillate fuels and fuel oils.

It is to be understood, however, that the compositions contemplated herein can also contain other materials. For example, corrosion inhibitors, extreme pressure agents and the like can be used as exemplified respectively by metallic phenates sulfonates, polymeric succinimides, non-metallic or metallic phosphorodithioates and the like. These materials do not detract from the value of the compositions of this invention, rather the materials serve to impart their customary properties to the particular compositions in which they are incorporated.

The following examples are merely illustrative and not meant to be limitations.

EXAMPLES

Example 1

Two equivalents of an alkenylsuccinic anhydride (obtained by reacting 920 MW polyisobutylene with maleic anhydride) was aminated with one equivalent of tetraethylenepentamine (TEPA) to give an alkylene substituted bis-succinimide. One equivalent of the above succinimide, one equivalent of triethylamine, and toluene were charged into a reaction flask and stirred briefly. To this mixture, at ambient temperature, was added, dropwise, a slight excess of carbon disulfide, while maintaining the exothermic reaction temperature at about 40° C. After the addition was complete, the reaction mixture was stirred at about 40° C. for one hour. The triethylammonium salt of the succinimide-substituted dithiocarbamic acid thus formed was then heated to 60° C. and treated dropwise with a slight excess of butylene oxide to form the corresponding beta-hydroxyalkyl ester. After cooling to 40° C., a slight excess of boric acid was charged in portions to the reaction mixture, a Dean-Stark trap was attached, and the reaction mixture was then heated slowly to reflux temperatures. The reaction was completed when no more water was collected during azeotropic distillation. It may not be necessary to perform the reaction to completion, but completion is often preferred. After cooling to ambient temperature, the reaction mixture was diluted with toluene, filtered over celite and the filtrate stripped of solvent to give the product.

The reaction can be performed with other polyamine-derived bis or mono-alkyl- or alkenylsuccinimides, which contain at least one basic secondary amine, in other aprotic solvents such as hexanes, xylene, ethers, etc. Similarly, other hydrocarbylene oxides, e.g., ethylene oxide, propylene oxide, styrene oxide, etc. may be used. The succinimides and carbon disulfide may be used in equimolar amounts if the alkyl- or alkenylsuccinimide contains only one basic secondary nitrogen or more than one equivalent amount of carbon disulfide depending on the number of basic secondary nitrogens present.

Following the procedure of Example 1, but varying the alkylene-succinimides and/or the olefin oxide, the products of the examples given below were prepared in mostly quantitative yields.

Example 2

The product of this example was prepared by the above general procedure of Example 1, using the bis-succinimide obtained from the amination of $C_{18}$–$C_{24}$ alkenylsuccinic anhydride with diethylenetriamine (DETA) and with epoxyhexadecane (Vikolox 16, Viking Chemical Co.) as the alkylene oxide.

Example 3

This product was obtained following the general procedure of Example 1, using the bis-succinimide obtained from aminating two equivalents of $C_{18}$–$C_{24}$ succinic anhydride with tetraethylenepentamine (TEPA) and with epoxyhexadecane (Vikolox 16) as the alkylene oxide.

Example 4

Same reaction as Example 2, with propylene oxide as the reactant alkylene oxide.

Example 5

This product was obtained by the procedure of Example 1, using the monosuccinimide prepared by aminating $C_{18}$–$C_{24}$ alkenylsuccinic anhydride with N-octadecenylaminopropylamine and with propylene oxide as the alkylene oxide.

Example 6

Same reaction as Example 3, but butylene oxide was the alkylene oxide used.

Example 7

Same reactants were used as in Example 3 except that propylene oxide was the alkylene oxide used.

EVALUATION OF PRODUCTS

The additives were blended (1%) into a solvent refined paraffinic neutral base stock and tested for antioxidant effectiveness by the Catalytic Oxidation test and for antiwear activity in the standard Four-Ball Wear Test machine. The conditions of the tests, results and comparison of the above products with the base oils in which they were blended are shown in Tables 1 and 2 below.

The results demonstrate the remarkable antioxidant features of the examples with respect to control of the increase in viscosity and acidity. The Catalytic Oxidation Test may be summarized as follows: Basically the lubricant is subjected to a stream of air which is bubbled through the oil formulation at the rate of five liters per hour at 325° F. for 40 hours. Present in the composition are samples of metals commonly used in engine construction, namely iron, copper, aluminum and lead, see U.S. Pat. No. 3,682,980 incorporated herein by reference for further details.

TABLE 1

Catalytic Oxidation Test
325° F., 40 hrs.

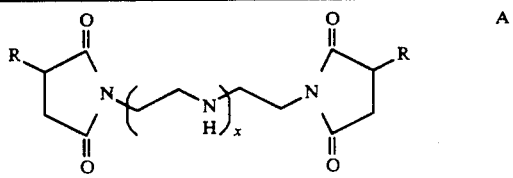

TABLE 1-continued

Catalytic Oxidation Test
325° F., 40 hrs.

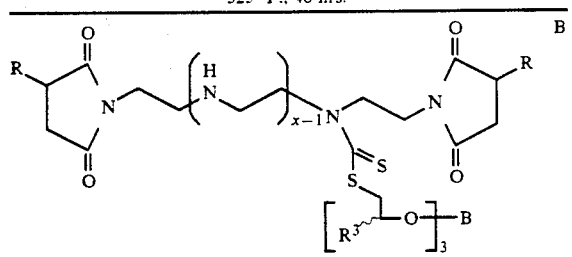

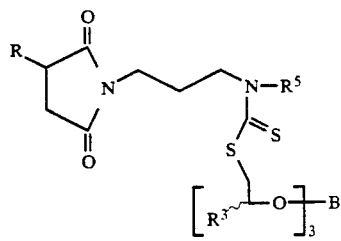

| Item | Additive (1%) | ΔNN | % ΔKV | Pb Loss (mg) |
|---|---|---|---|---|
| 1 | None (100% solvent refined paraffinic neutral lubricating oil) | 12.1 | 141.5 | 7.7 |
| 2 | A: Underivatized Succinimide: R = 920 m.w. PIB; x = 3 | 8.0 | 152.5 | 7.7 |
| 3 | A: Underivatized Succinimide: R = $C_{18}$-$C_{24}$ mix; x = 3 | 7.9 | 47.0 | 4.4 |
| 4 | Ex. 1; B: R = 920 m.w. PIB; $R^3$ = $C_2H_5$; x = 3 | 2.3 | 42.0 | 1.0 |
| 5 | Ex. 2; B: R = $C_{18}$-$C_{24}$ mix; $R^3$ = $C_{14}H_{29}$; x = 1 | 1.1 | 7.4 | 0.4 |
| 6 | Ex. 3; B: R = $C_{18}$-$C_{24}$ mix; $R^3$ = $C_{14}H_{29}$; x = 3 | 0.1 | 12.7 | 0.8 |
| 7 | Ex. 4; B: R = $C_{18}$-$C_{24}$ mix; $R^3$ = $CH_3$; x = 1 | 5.8 | 31 | 0.0 |
| 8 | Ex. 5; C: R = $C_{18}$-$C_{24}$ mix; $R^3$ = $CH_3$; $R^5$ = $C_{18}H_{35}$ | 6.3 | 31.3 | 3.2 |
| 9 | Ex. 6; B: R = $C_{18}$-$C_{24}$ mix; $R^3$ = $C_2H_5$; x = 3 | 5.3 | 42 | 0.3 |
| 10 | Ex. 7; B: R = $C_{18}$-$C_{24}$ mix; $R^3$ = $CH_3$; x = 3 | 6.9 | 43.2 | 0.5 |

The Catalytic Oxidation Test results confirm the excellent control in both acidity and viscosity increase. These additives demonstrate remarkable antioxidant properties at only 1% concentration levels. They clearly outperform the underivatized succinimides shown as items 2 and 3 in Table 1 for comparison purposes.

The antiwear properties of the examples were also evaluated using the Four Ball Wear Test as shown in Table 2. The results clearly exhibit the excellent antiwear properties inherent in these unique compositions.

In the Four Ball Test three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 52100 steel for thirty minutes under 60 kg load at 2000 rpm and 200° F. If additional information is desired consult test method ASTM D2266 and/or U.S. Pat. No. 4,761,482.

TABLE 2

Four-Ball Wear Test
½" Balls, 52100 Steel, 60 kg, 2000 rpm, 200°F., 30 min.

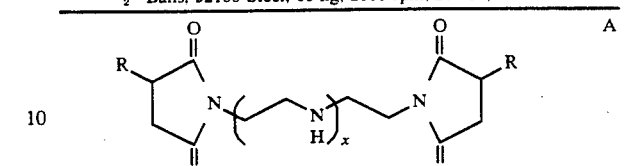

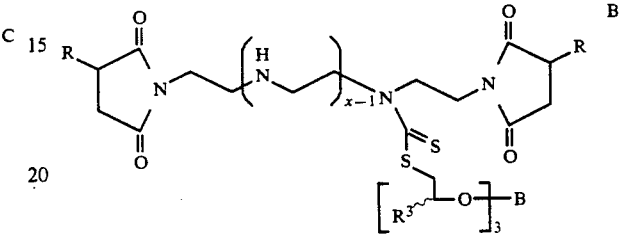

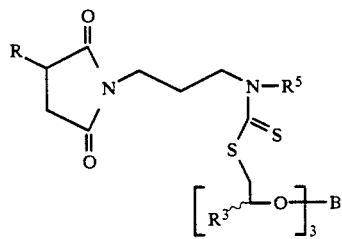

| Item | Additive (1%) | Wear Scar Diam (mm) |
|---|---|---|
| 1 | None (Base Oil) | 3.8 |
| 2 | A: Underivatized Succinimide: R = 920 m.w. PIB; x = 3 | 3.8 |
| 3 | A: Underivatized Succinimide: R = $C_{18}$-$C_{24}$ mix; x = 3 | 4.0 |
| 4 | B: R = $C_{18}$-$C_{24}$; $R^3$ = $C_{14}H_{29}$; x = 3 | 2.0 |
| 5 | C: R = $C_{18}$-$C_{24}$; $R^3$ = $CH_3$; $R^5$ = $C_{18}H_{35}$ | 0.67 |
| 6 | B: R = $C_{18}$-$C_{24}$; $R^3$ = $CH_3$; x = 1 | 0.70 |
| 7 | B: R = $C_{18}$-$C_{24}$; $R^3$ = $C_{14}H_{29}$; x = 1 | 1.9 |

The Four-Ball Wear Test results demonstrate the excellent antiwear properties of these compositions when used at only 1% concentration in mixed mineral oils.

The above table shows that the products of this invention clearly outperform the underivatized dispersants (Items 2 and 3) in providing antiwear protection in addition to dispersancy to the lubricant base oil.

The described unique dithiocarbamates can be effectively used in synthetic oils and mixtures of synthetic oils and mineral oils. Useful lubricant oil compositions include gear oils, marine oils, aviation oils, hydraulic oils and turbine oils.

The foregoing data demonstrate the multifunctional antiwear/antioxidant effectiveness, at low concentrations, of the borated hydroxyalkyl esters of alkyl or alkenylsuccinimide-substituted dithiocarbamic acids in lubricant compositions. These novel ashless and non-phosphorus additives will significantly enhance the stability and performance of premium quality automotive and industrial lubricants and greases. In addition, they do not contain environmentally and toxicologically undesirable metals or other potentially undesirable elements. This and their performance characteristics as demonstrated by their multifunctional effectiveness in lubricant compositions will enhance their application and market acceptability.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

What is claimed is:

1. A composition comprising a major proportion of an oil of lubricating viscosity or a grease prepared therefrom and a minor multifunctional amount of an additive product comprising borated derivatives of beta-hydroxyhydrocarbyl esters of alkyl or alkenylsuccinimide-substituted dithiocarbamic acids.

2. The composition of claim 1 wherein the borated beta-hydroxyhydrocarbyl esters have the following generalized structure:

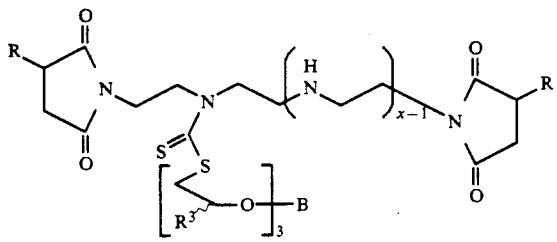

wherein R is $C_8$ to about $C_{10,000}$ hydrocarbyl or mixtures thereof, $R^3$ is H or $C_1$ to about $C_{100}$ hydrocarbyl and x equals 3.

3. The composition of claim 2 wherein $R=C_{18}$ to about $C_{24}$.

4. The composition of claim 2 wherein said beta-hydroxy-hydrocarbyl esters are prepared in the following manner: (1) alkyl- or alkenyl-substituted succinimides are first prepared by aminating the corresponding anhydrides with polyamines; (2) reacting the resultant succinimides with carbon disulfide in the presence of a tertiary amine in an organic solvent to obtain the quaternary amine salt of the corresponding succinimide-substituted dithiocarbamic acid; (3) reacting these salts with hydrocarbylene oxides to obtain the desired beta-hydroxyhydrocarbyl esters; (4) and thereafter borating said esters.

5. The composition of claim 4 wherein said anhydride is a $C_{18}$-$C_{24}$ alkyl- or alkenylsuccinic anhydride; the polyamine is selected from the group consisting of tetraethylenepentamine, diethylenetriamine and N-octadecenylaminopropylamine; the tertiary amine is selected from $C_1$ to about $C_{12}$ trialkylamines; the solvent is selected from the group consisting of toluene, hexanes, xylenes or ethers; the hydrocarbylene oxide is selected from the group consisting of butylene oxide, propylene oxide, ethylene oxide and styrene oxide and wherein the resultant beta-hydroxyhydrocarbyl esters are borated with boronating compounds selected from the group consisting of boric acid, metaboric acid, metaborates, alkyl boroxines, boroxine and boroxides.

6. The composition of claim 4 wherein said anhydride is a $C_{18}$-$C_{24}$ alkyl- or alkenylsuccinic anhydride, the polyamine is selected from the group consisting of tetraethylenepentamine, diethylenetriamine and N-octadecenylaminopropylamine, the tertiary amine is triethylamine, the solvent is toluene, the hydrocarbylene oxide is selected from the group consisting of butylene oxide, propylene oxide and epoxyhexadecane and wherein the resultant beta-hydroxyhydrocarbyl esters are borated with boric acid.

7. The composition of claim 2 wherein said alkenylsuccinic anhydride is prepared by reacting 920 MW polyisobutylene with maleic anhydride.

8. The composition of claim 1 wherein said major proportion comprises an oil of lubricating viscosity selected from the group consisting of (1) mineral oils (2) synthetic oils or mixture of synthetic oils, (3) a mixture of (1) and (2) and (4) a grease prepared from any one of (1), (2) or (3).

9. The composition of claim 8 wherein the lubricant is a mineral oil as defined in (1).

10. The composition of claim 8 wherein the lubricant is a synthetic oil as defined in (2).

11. The composition of claim 8 wherein the lubricant is a mixture of oils as defined by (3).

12. The composition of claim 7 wherein the lubricant is a grease prepared from any one of (1), (2) or (3) or mixtures thereof.

13. A process for making lubricant additive products of reaction consisting of borated beta-hydroxyhydrocarbyl esters of alkyl or alkenylsuccinimide-substituted dithiocarbamic acids, comprising (1) reacting alkyl- or alkenylsuccinimides with carbon disulfide in the presence of a tertiary amine in an organic solvent to obtain the quaternary amine salt of the correcting succinimide-substituted dithiocarbamic acid; (2) reacting the resulting salts with hydrocarbylene oxides to obtain the desired beta-hydroxyhydrocarbyl esters; (3) and thereafter borating said esters and wherein the molar ratio of succinic anhydride to polyamine varies from 2 to 1, to 1 to 1 and the molar ratio of carbon disulfide and tertiary amine to succinimide varies from 1 to x per mole of succinimide, x is equal to 1 to 10, under ambient or autogenous pressure at temperatures varying from about 40° C. to about 80° C.

14. The process of claim 13 wherein the borated beta-hydroxyhydrocarbyl esters have the following generalized structure:

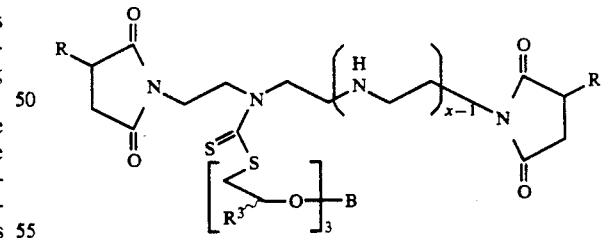

wherein $R=C_8$ to about $C_{10,000}$ hydrocarbyl or a mixture thereof, $R^3$ is H or $C_1$ to about $C_{100}$ hydrocarbyl and $x=3$.

15. The process of claim 14 wherein said alkyl- or alkenylsuccinimide is prepared from a $C_{18}$-$C_{24}$ alkyl- or alkenylsuccinic anhydride and a polyamine selected from the group consisting of tetraethylenepentamine, diethylenetriamine and N-octadecenylaminopropylamine; the tertiary amine is selected from trialkylamines; the solvent is selected from the group consisting of toluene, hexanes, xylenes or ethers; the hydrocarbylene oxide is selected from the group consisting of butylene oxide, propylene oxide, ethylene oxide and styrene oxide and wherein the resultant beta-hydroxyhydrocarbyl esters are borated with boronating compounds selected from the group consisting of boric acid, metaboric acid, metaborates, alkyl boroxines, boroxine and boroxides.

16. The process of claim 13 wherein $R = C_{18}$ to about $C_{24}$.

17. The process of claim 16 wherein said anhydride is a $C_{18}$–$C_{24}$ alkyl- or alkenylsuccinic anhydride, the polyamine is selected from the group consisting of tetraethylenepentamine, diethylenetriamine and N-octadecenylaminopropylamine, the tertiary amine is triethylamine, the solvent is toluene, the alkylene oxide is selected from the group consisting of butylene oxide and propylene oxide and wherein the resultant beta-hydroxyhydrocarbyl esters are borated with boric acid.

18. The process of claim 14 wherein said an alkenylsuccinic anhydride is prepared by reacting 920 MW polyisobutylene with maleic anhydride.

19. A method of reducing fuel consumption in an internal combustion engine which comprises (1) lubricating said engine with a composition comprising a major proportion of a lubricating oil and a fuel reducing/multifunctional additive amount of a product of reaction obtained by (1) reacting an alkyl- or alkenylsuccinimide with carbon disulfide in the presence of a tertiary amine and an organic solvent, obtaining the quaternary amine salt of the corresponding succinimide-substituted dithiocarbamic acid; (2) reacting said salt with a hydrocarbylene oxide to obtain the beta-hydroxyhydrocarbyl esters; (3) and thereafter borating said esters and wherein the molar ratio of succinic anhydride to polyamine varies from 2 to 1, to 1 to 1 and the molar ratio of carbon disulfide and tertiary amine to succinimide varies from 1 to x per mole of succinimide, x is equal to 1 to 10, under ambient or autogenous pressure at temperatures varying from about 40° C. to about 80° C.

* * * * *